NEOREGELIA PLANT
Filed July 16, 1975
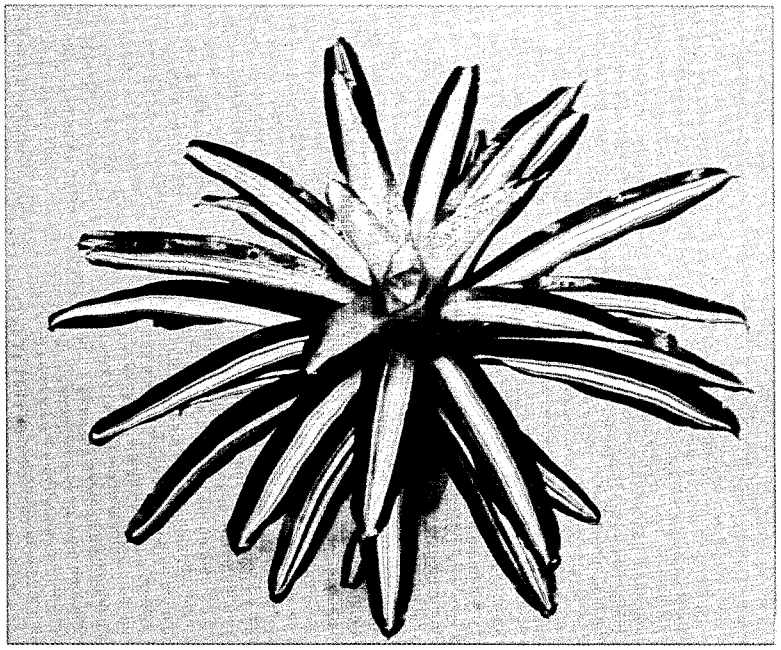

United States Patent

Plant Pat. 3,971
Patented Nov. 2, 1976

3,971
NEOREGELIA PLANT

Paul de Coster, Ruitersdreef 1, Melle, B-9230 Belgium, and Adrien Simoens, Zonneveld 21, Merelbeke, B-9220 Belgium Filed July 16, 1975, Ser. No. 596,441
Int. Cl.[2] A01H 5/00
U.S. Cl. Plt. 88 1 Claim The present invention relates to a new bromeliad cultivar, which is a sport of *Neoregelia carolinae*. The new cultivar possesses characteristics which make the plant distinctive from *Neoregelia carolinae* var. tricolor, the botanical variety which is cultivated in great quantities.

Growers have constantly tried to control the characteristics of young plants obtained by the sowing of the parent cultivar *Neoregelia carolinae* Marechalii. The very peculiar characteristics of this cultivated plant were noticed for the first time in 1968. The cultivated plant comprising the present invention is a mutation of *Neoregelia carolinae* Marechalii and flowered for the first time in 1970. The mutation appeared regularly in all of the plants which were obtained by taking side-shoots from the mother-plant.

Strict and repeated selections and asexual propagation of such selections in Belgium have demonstrated that the new cultivar propagates true to type through successive generations.

A description of the unique characteristics of the new cultivar are as follows:

(1) The magnificent yellow-colored mutation of the chlorophyll in the leaf. The new cultivar possesses many of the characteristics of the parent variety, namely, compact growth, broad leaves, quick growing, good color of the bracts, with long tenability.

(2) In naturally-flowered plants the rosette is comprised of some thirty leaves each having a width of about 5 cm. and average length of 27.5 cm. The *Neoregelia carolinae* var. tricolor has a leaf width of 3.25 cm. and a leaf length of 38.5 cm., so the leaf width of the new cultivar is nearly twice that of the comparison cultivar). All of the leaves of the new cultivar show in the center thereof, along the lengthwise axis, a cream-yellow stripe, RHS Color Chart 4 D, Yellow Group, with a width of 2.5 to 3 cm.; this stripe may show fine green lines.

(3) With regard to the inflorescence and the color of the bracts of the new cultivar, at flowering there appears a complete red coloring, RHS Color Chart, 53A–D, Red Group, with the sheen at times imparting more of a red appearance, for about six heart leaves, while certain of the yellowish stripes of the following leaves (about five in number) show a pink-red coloring when the plants are grown in sufficiently lighted location. As for the parent cultivar *Neoregelia carolinae* Marechalii, the inflorescence is by itself of little importance as a decorative feature, as it remains in the funnel between the red-colored bracts. The flowers of the new cultivar are similar to those of the parent cultivar.

Asexual reproduction of the new cultivar is made exclusively by taking side-shoots which are formed in rapid sequence from the leaf axils after the plant has flowered.

When comparing the new cultivar with the cultivar *Neoregelia carolinae* var. tricolor, the following distinctive characteristics are clearly noticed:

(1) Relatively broad leaves (5 cm. instead of 3 cm. for *Neoregelia carolinae* var. tricolor).

(2) A wider, central stripe (2.5 cm. compared with 1 to 1.5 cm. for *Neoregelia carolinae* var. tricolor.)

(3) Large number of side-shoots in quick sequence (15 side-shoots in 18 months compared with 10–12 in the same time period for *Neoregelia carolinae* var. tricolor).

(4) Easy flower-induction, even in young plants (offshoots of six months artificially induced by acetylene treatment give very good color, as compared with *Neoregelia carolinae* var. tricolor which needs at least 12 months before flower induction leads to sufficient red coloring).

(5) Compact growth (length-width proportion is 5/1 for the new cultivar, length 25 cm., width 5 cm., as compared to the 10/1 length-width proportion of *Neoregelia carolinae* var. tricolor, length 38 cm., width 3.25 cm. The total diameter of the leaves—rosette is at least 10 cm. less, and the highly colored bracts of the new cultivar extend to approximately the same height as the green and cream yellow bracts.

The above noted characteristics of the new cultivar are illustrated in the accompanying color photographic drawing, which depicts the true colors of the cultivar as closely as possible with color illustrations of this type.

We claim:

1. A new cultivar, of Neoregelia characterized by its broader leaves; a more compact plant rosette comprised of some thirty leaves with a width of about 5 cm. which have in the middle along the lengthwise axis, a cream white stripe 2.5 to 3 cm. wide, sometimes with very fine green lines therethrough; inflorescence in the form of red coloring of about six bracts, while certain of said cream-white stripes of the lowermost leaves display a pink-red coloring.

References Cited

Alberts & Merkel Bros., Inc. catalog for 1963, Boynton Beach, Fla., pp. 52, 58 relied on.

Exotica 3, Graf, Rohrs Co., Rutherford, N.J., 1963, 436, 1659 relied on.

Johnson Cactus Gardens catalog for 1968, Paramount, CA, p. 44 relied on.

ROBERT E. BAGWILL, Primary Examiner

UNITED STATES PATENT AND TRADEMARK OFFICE

CERTIFICATE OF CORRECTION

PATENT NO. : PLANT PATENT 3971
DATED : NOVEMBER 2, 1976
INVENTOR(S) : Paul De Coster et al.

It is certified that error appears in the above-identified patent and that said Letters Patent are hereby corrected as shown below:

In the heading of the patent, column 1, approximately line 8, the following information should be inserted:

Foreign Application Priority Data

Jan. 13, 1975, Belgium . . . . . PVO/152.338

Signed and Sealed this

Twelfth Day of April 1977

[SEAL]

*Attest:*

RUTH C. MASON
*Attesting Officer*

C. MARSHALL DANN
*Commissioner of Patents and Trademarks*

UNITED STATES PATENT AND TRADEMARK OFFICE

CERTIFICATE OF CORRECTION

PATENT NO. : PP. 3,971

DATED : November 2, 1976

INVENTOR(S) : Adrien Simoens

It is certified that error appears in the above-identified patent and that said Letters Patent is hereby corrected as shown below:

On the title page, lines 3 and 4 delete "Paul de Coster, Ruitersdreef 1, Melle, B-9230 Belgium, and".

Signed and Sealed this

*Ninth* Day of *April 1985*

[SEAL]

*Attest:*

DONALD J. QUIGG

*Attesting Officer* *Acting Commissioner of Patents and Trademarks*

REEXAMINATION CERTIFICATE (345th)

United States Patent [19]

de Coster et al.

[11] B1 Plant 3,971

[45] Certificate Issued May 14, 1985

[54] NEOREGELIA PLANT

[76] Inventors: Paul de Coster, Ruitersdreef 1, Melle, B-9230; Adrien Simoens, Zonneveld 21, Merelbeke, B-9920, both of Belgium

Reexamination Request:
No. 90/000,557, May 16, 1984

Reexamination Certificate for:

| | |
|---|---|
| Patent No.: | **Plant 3,971** |
| Issued: | **Nov. 2, 1976** |
| Appl. No.: | **596,441** |
| Filed: | **Jul. 16, 1975** |

Certificate of Correction issued Apr. 12, 1977.

[30] Foreign Application Priority Data

Jan. 13, 1975 [BE] Belgium ..... PVO/152.338

[51] Int. Cl.[3] ..... A01H 5/00

[52] U.S. Cl. ..... Plt./88

[58] Field of Search ..... Plt./88

[56] References Cited

PUBLICATIONS

The Bromeliad Society Bulletin XIII, Nov.-Dec. 1963, No. 6.

The Bromeliad Society Bulletin, vol. VI, Nov.-Dec. 1956, No. 6.

*Primary Examiner*—Robert E. Bagwill

EXEMPLARY CLAIM

1. A new cultivar, of Neoregelia characterized by its broader leaves; a more compact plant rosette comprised of some thirty leaves with a width of about 5 cm. which have in the middle along the lengthwise axis, a cream white stripe 2.5 to 3 cm. wide, sometimes with very fine green lines therethrough; inflorescence in the form of red coloring of about six bracts, while certain of said cream-white stripes of the lowermost leaves display a pink-red coloring.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

* * * * *